(12) United States Patent
Rokicki

(10) Patent No.: US 9,017,489 B2
(45) Date of Patent: *Apr. 28, 2015

(54) METHOD FOR SURFACE INCLUSIONS DETECTION, ENHANCEMENT OF ENDOTHELIAL AND OSTEOBLAST CELLS ADHESION AND PROLIFERATION, STERILIZATION OF ELECTROPOLISHED AND MAGNETOELECTROPOLISHED NITINOL SURFACES

(76) Inventor: Ryszard Rokicki, Emmaus, PA (US)

( * ) Notice: Subject to any disclaimer, the term of this patent is extended or adjusted under 35 U.S.C. 154(b) by 601 days.

This patent is subject to a terminal disclaimer.

(21) Appl. No.: 13/373,814

(22) Filed: Dec. 1, 2011

(65) Prior Publication Data

US 2012/0093944 A1 Apr. 19, 2012

Related U.S. Application Data

(63) Continuation-in-part of application No. 12/660,904, filed on Mar. 5, 2010, now Pat. No. 8,377,237.

(60) Provisional application No. 61/214,380, filed on Apr. 23, 2009.

(51) Int. Cl.

| | |
|---|---|
| *C22F 1/10* | (2006.01) |
| *A61F 2/01* | (2006.01) |
| *A61F 2/02* | (2006.01) |
| *A61M 25/00* | (2006.01) |
| *A61B 17/03* | (2006.01) |
| *A61B 17/04* | (2006.01) |
| *A61L 27/06* | (2006.01) |
| *A61B 17/12* | (2006.01) |
| *A61B 19/00* | (2006.01) |
| *A61L 29/02* | (2006.01) |
| *A61L 31/02* | (2006.01) |
| *C22C 19/00* | (2006.01) |
| *C22C 19/03* | (2006.01) |
| *G01N 33/20* | (2006.01) |
| *A61B 17/064* | (2006.01) |
| *A61B 17/32* | (2006.01) |
| *A61B 17/00* | (2006.01) |
| *A61F 2/24* | (2006.01) |
| *A61F 2/82* | (2013.01) |

(52) U.S. Cl.
CPC ............ *A61L 27/06* (2013.01); *A61B 17/12113* (2013.01); *A61B 17/1214* (2013.01); *A61B 19/34* (2013.01); *A61L 29/02* (2013.01); *A61L 31/022* (2013.01); *C22C 19/007* (2013.01); *C22C 19/03* (2013.01); *G01N 33/20* (2013.01); *A61B 17/0401* (2013.01); *A61B 17/064* (2013.01); *A61B 17/12022* (2013.01); *A61B 17/32* (2013.01); *A61B 2017/00526* (2013.01); *A61B 2017/00867* (2013.01); *A61F 2/24* (2013.01); *A61F 2/82* (2013.01)

(58) Field of Classification Search
CPC ................................. C22C 19/03; C22F 1/006
USPC ................. 148/402; 623/1.13, 1.15; 604/264; 606/200, 228, 219
See application file for complete search history.

(56) References Cited

U.S. PATENT DOCUMENTS 7,632,390 B2    12/2009    Rokicki
8,377,237 B2 *    2/2013    Rokicki ........................ 148/402

OTHER PUBLICATIONS

Morgan, N. B. "Medical shape memory alloy applications—the market and its products." Materials Science and Engineering: A 378.1 (2004): 16-23.*
Svetlana Shabalovskaya, et al. "Comparative corrosion performance of black oxide, sandblasted and fine-drawn Nitinol wires in potentiodynamic and potentiostatic tests: Effect of chemical etching and electropolishing" Journal of Biomedical Research Part B: Applied Biomaterials, vol. 69B,Issue 2, pp. 223-231, May 15, 2004.
G. Siekmeyer, et al. "The fatigue behavior of different Nitinol stent tubes characterized by micro dog-bone testing" ASM-Conference, Sep. 23-25, 2007 Palm Desert (CA).
Ryszard Rokicki "Detecting Nitinol surface inclusions" Medical Device& Diagnostic Industry, Feb. 2010, p. 44-48, Canon Communication LLC Publication, Los Angeles, CA.
Rokicki, Ryszard, Detecting Nitinol Surface Inclusions, Medical Device and Diagnostic News (http://www.mddionline.com), Feb. 1, 2010.
Shabalovskaya, Svetlana, et al., Comparative Corrosion Performance of Nitinol Wires with Black Oxide, Sand Blasted and Fine-drawn in Potentiodynamic and Potentiostatic Tests: Effects of Chemical Etching and Electropolishing; Journal of Biomedical Materials Research Part B: Applied Biomaterials, vol. 69B, Issue 2, pp. 231-233, May 14, 2004.
Siekmeyer, G., et al., The Fatigue Behaviour of Different Nitinol Stent Tubes Characterized by Micro Dog-Bone Testing, ASM Conference, Palm Desert, CA, Sep. 23-25, 2007.

* cited by examiner

*Primary Examiner* — Jessee Roe
(74) *Attorney, Agent, or Firm* — Sanford J. Piltch

(57) ABSTRACT

The method for surface inclusions detection, enhancement of endothelial and osteoblast cells adhesion and proliferation and sterilization of electropolished and magnetoelectropolished Nitinol implantable medical device surfaces uses an aqueous solution of chemical compounds containing halogenous oxyanions as hypochlorite ($ClO^-$) and hypobromite ($BrO^-$) preferentially 6% sodium hypochlorite (NaClO).

18 Claims, 3 Drawing Sheets

METHOD FOR SURFACE INCLUSIONS DETECTION, ENHANCEMENT OF ENDOTHELIAL AND OSTEOBLAST CELLS ADHESION AND PROLIFERATION, STERILIZATION OF ELECTROPOLISHED AND MAGNETOELECTROPOLISHED NITINOL SURFACES

CROSS REFERENCE TO RELATED APPLICATIONS

This application is a continuation-in-part and claims the benefit of priority to U.S. patent application Ser. No. 12/660,904, now U.S. Pat. No. 8,377,237, with a filing date of Mar. 5, 2010, which claims priority to U.S. provisional application No. 61/214,380, filed Apr. 23, 2009.

BACKGROUND OF THE INVENTION

The present invention relates to the field of chemical testing, modifying the surface of a material to promote enhancement of endothelial and osteoblast cells monolayer coverage and sterilization of intermetallic materials. More specifically, it is for testing, surface modifying and sterilization of the electropolished and magnetoelectropolished nickel titanium intermetallic compound known as Nitinol.

The purpose of this test is the detection of Nitinol surface inclusions (except for titanium dioxides $TiO_2$ native inclusions originated during melting process, which do not dissolve in sodium hypochlorite (NaClO) and are harmless to endothelial and osteoblast cells, but still can be the fracture initiation sites), which are indicators of the lack of chemical homogeneousness of the surfaces by immersing electropolished or magnetoelectropolished Nitinol surfaces in an aqueous solution of sodium hypochlorite (NaClO) and checking for black flocculent precipitate developing on the particular surface site.

Simultaneously, the electropolished and magnetoelectropolished Nitinol surfaces, which lack surface inclusions (except titanium dioxide $TiO_2$ native inclusions), undergo chemical modification which leads to better and faster endothelial and osteoblast cells monolayer formation. The surface modification by chemical treatment with sodium hypochlorite (NaClO) promotes endothelial (vascular implantable devices) and osteoblast (orthopedic implantable devices) cell adhesion and proliferation on implantable electropolished and magnetoelectropolished Nitinol devices.

The electropolished and magnetoelectropolished Nitinol surfaces which underwent the sodium hypochlorite treatment without detection of intermetallic surface inclusion (except titanium dioxide $TiO_2$ native inclusions) are sterile and ready for implantation.

The site or sites where this black flocculent precipitate starts to develop is the place of surface inclusion and gives evidence of the lack of homogeneousness of the Nitinol surface, which is a sign of inferiority and should be the base for rejection of such electropolished or magnetoelectropolished Nitinol implantable devices.

The surface inclusions cause maximum stress during bending-rotation and flexing, especially in peripheral stents, and lead to their fracture. Also, inclusions are themselves source sites where corrosion starts to dissolve matrix materials releasing nickel ions harmful to living cells surrounding a particular implantable device.

The Nitinol inclusions can be classified in two ways: by their origin and by their chemical composition. The classification by origin gives two kinds of inclusions: native, which originate during production of bulk material, and foreign, introduced during finishing operations.

The native inclusions are randomly distributed through the whole volume of material and finding them on the surface of a nitinol implantable medical device which underwent electropolishing or magnetoelectropolishing (except titanium dioxides $TiO_2$ native inclusions) should validate rejection of such device. In contrast, foreign inclusions are strictly surface phenomenae introduced to the surface during finishing operations as: glass-bead, sand or aluminum oxide blasting, heat treatment, mechanical polishing, lapping, laser cutting, drawing, electro discharge machining etc.

The classification by chemical composition is more complicated. Taking under consideration the very small size of inclusions the chemical analysis is often difficult and very often leads to errors. Those inclusions could be broadly classified as carbides (TiC), oxides ($Ti_4N_2O_x$, $TiO_2$) or intermetallic precipitates ($Ni_4Ti_3$).

It is widely recognized that carbides are created during (VIM) vacuum induction melting from carbon crucibles used in this process. On the other hand, oxides are originated in a higher amount and in a larger particle size during (VAM) vacuum arc melting. The third process which claims four to ten times lower carbon content due to use of water cooled crucibles is (EBM) electron beam melting.

Regardless of the above Nitinol production methods, not one of them is perfect and in the present time it isn't possible to produce 100% inclusions free, homogenous Nitinol.

Until now the only ways to check up the Nitinol surface for inclusions were microscopic and instrumental methods as: scanning electron microscope (SEM) with energy dispersive X-ray (EDX) spectrometry, atomic force microscopy (AFM), transmission electron microscopy (TEM) X-ray diffraction, and Auger spectrometer with back-scatter electron detector (BSE).

All of those above mentioned techniques are very expensive, time consuming, demanding highly trained operators and by this they are excellent techniques for scientific research or limited industrial inspections, but unpractical for large scale production inspections.

Because the present invention is very simple, inexpensive, very effective (almost 100%), doesn't require expensive instrumentation and highly trained operators and can be applied to every single electropolished or magnetoelectropolishd implantable medical devices, it is perfectly suited for mass inspections.

The post production test of finished products can eliminate defective products which have avoided detection during raw material testing, because inclusions were not present on the surface during initial test and appear on the surface as a results of production operations: removing excess material by mechanical, chemical or electrochemical processes and revealing inclusions from the bulk of material or by introducing externally new inclusions to the surface of finished products as a result of manufacturing operations as laser cutting, sand blasting, drawing etc.

By applying post production lots testing, very serious (fracture of endodontic rotary file for example) and even life-threatening problems (as for example fracture of carotid stent or heart valve) could be avoided.

BRIEF SUMMARY OF THE INVENTION

The present invention relates to a method for detection of surface inclusions, enhancement of endothelial and osteoblast cell adhesion, and proliferation and sterilization of electropolished and magnetoelectropolished implantable Nitinol medical devices surfaces. The overlooked surface inclusions on electropolished or magnetoelectropolished Nitinol implantable medical device surfaces could lead to very undesirable consequences as fractures, enhanced corrosion behavior, lower or diminished bio, and hemcompatibility of medical implantable devices and medical and dental instruments.

Simultaneously electropolished or magnetoelectropolished implantable Nitinol medical devices lacking surface inclusion (except titanium dioxide $TiO_2$ native inclusions) undergo chemical surface modification (enhanced oxidation to the depth of about 13 nm) which correlates with better and faster endothelial and osteoblast cells adhesion and proliferation. At the same time sterilization of submerged surfaces takes place.

BRIEF DESCRIPTION OF THE DRAWINGS

FIG. 2A-2D are micrographs of osteoblast cell after three days of incubation on: FIG. 2A—electropolished (EP) surface, FIG. 2B—electropolished (EP)+6% NaClO treated surface, FIG. 2C—magnetoelectropolished (MEP) surface, 2D—magnetoelectropolished (MEP)+6% NaClO treated surface of Nitinol.

DESCRIPTION OF THE INVENTION

Figure 1A:
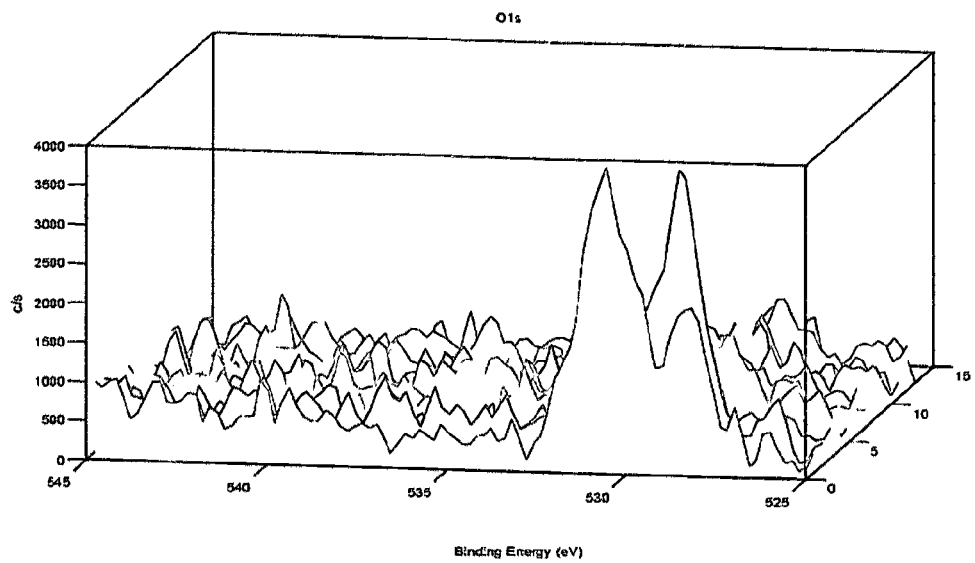
FIG. 1A-1D are XPS oxygen depth profile graphs of oxide on: 1A—electropolished (EP) surface, 1B—electropolished (EP)+6% NaClO treated surface, 1C—magnetoelectropolished (MEP) surface, 1D—magnetoelectropolished (MEP)+6% NaClO treated surface of Nitinol.

In recent years the usage of Nitinol, an almost equiatomic binary intermetallic compound of nickel and titanium, has been steadily growing. The main fields in which Nitinol is finding more and more application are the medical and dental devices markets. Nitinol medical devices can be divided into two main groups: one consisting of implantable devices, for example peripheral stents, cardiovascular luminal shields, heart valves etc, and another including the tools and instruments used during medical procedures as stone and blood clots retrievers, vena cava filters, endoscopes, etc. The dental devices are endodontic rotary files, orthodontic archwires, etc.

The main reason for the growing usage of Nitinol arises from a remarkable combination of mechanical (pseudoplasticity and shape memory) and biocompatible properties. The unusual mechanical properties of Nitinol are due to its ability to undergo reversible change between two crystals structures.

The good biocompatibility originates from its chemical composition. The very high content of titanium is responsible for the spontaneous creation of very rich titanium oxide, which is also present on commercially pure titanium and another titanium containing alloys.

The quest to develop almost totally homogenous, inclusions free Nitinol, with improved fatigue and corrosion resistance properties, continues. Among the new approaches to achieve this goal are: smart anodization, acidic and basic chemical etching, heat treatment in different gaseous atmospheres, ion implantation, cryogenic treatment, electropolishing and the latest proposed magnetoelectropolishing process (U.S. Pat. No. 7,632,390).

However, all of the above mentioned methods with their claimed and actual working properties are destined to failure as long as finished Nitinol products will not be surface inclusions free.

Even the electropolishing process which is recognized as the gold standard for finishing Nitinol implantable medical devices could leave inclusions of different chemical natures on the surface after termination of the electropolishing treatment alongside with obviously occurring and biologically harmless titanium dioxides $TiO_2$ inclusions. Svetlana Shabalovskaya, et al. "Comparative corrosion performance of black oxide, sandblasted and fine-drawn Nitinol wires in potentiodynamic and potentiostatic tests: Effect of chemical etching and electropolishing." Journal of Biomedical Materials Research Part B: Applied Biomaterials, Vol. 69B, Issue 2, pages 233-231, 15 May 2004

It is well documented that about 80% of crack initiation in Nitinol stents are triggered by surface inclusions. G. Siekmeyer, et al. "The fatigue behavior of different Nitinol stent tubes characterized by micro dog-bone testing" ASM-Conference, Sep. 23-25, 2007 Palm Desert (CA), USA. The best evidence about the importance of this problem is fact that Nitinol producers are offering now Extra Low Inclusion Nitinol (EUROFLEX, Nitinol SE 508 ELI).

The main inclusions identified in Nitinol are titanium carbides (TiC), which are introduced to Nitinol mainly during vacuum induction melting (VIM) and originate from carbon crucibles used during the melting process. Another group of inclusions are oxidized intermetallics as $Ti_2NiO$ and oxides as $TiO_2$ introduce in larger amount during vacuum arc remelting (VAR) process.

Despite this, Nitinol surface inclusions are not a trivial matter, and cause many problems as corrosion, Ni leaching, fatigue initiation sites, local martensitic transformation and stress concentration points they haven't been studied too extensively till now.

The main ways to check the Nitinol surface for inclusions until now were instrumental techniques such as: transmission electron microscopy (TEM), Auger electron spectroscopy (AES) with back-scatter electron (BSC) detector, scanning electron microscopy (SEM) with energy dispersive X-ray (EDX) spectrometry, atomic force microscopy (AFM) and X-ray diffraction. All of these techniques are very expensive, time consuming, demanding very highly trained operators, sophisticated equipment and are not very effective and practical in mass inspection on an industrial scale.

The present invention overcomes these problems by giving a totally novel, cheap, more practical and almost 100% reliable method, which is not restricted by size or shape of tested electropolished or magnetoelectropolished Nitinol implantable medical devices for surface inclusions.

To my knowledge the present invention of testing Nitinol for surface inclusions by using sodium hypochlorite (NaClO) is totally new and never was employed or even mentioned in the prior art in this field.

As long as the interatomic bonds between Ni and Ti in Nitinol remain intact, the intermetallic compound will stay totally inert (except to chemical modification of the most outer oxide layer of the electropolished and magnetoelectropolished Nitinol which is enriched in oxygen beyond the starting level) when exposed to an aqueous of sodium hypochlorite (NaClO). But when those bonds are broken by precipitated inclusions, Nitinol becomes very prone to corrosion by sodium hypochlorite.

The mechanism of this corrosion arises from aggressiveness of NaClO toward Ni. When Ni metal is exposed to NaClO, a chemical reaction starts immediately and follows until all Ni is dissolved or NaClO is used according to reaction:

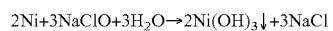

$$2Ni+3NaClO+3H_2O \rightarrow 2Ni(OH)_3\downarrow +3NaCl$$

The visual sign of this reaction is black flocculent precipitate of $Ni(OH)_3\downarrow$.

Even when Nitinol is broken when submerged in NaClO and broken surfaces don't contain inclusions, corrosion doesn't start, because freshly broken inclusion free surfaces are immediately oxidized by a very powerful oxidizer (NaClO) to $TiO_2$ which prevents corrosion.

But in the case when Nitinol possesses surface inclusions (except titanium dioxides $TiO_2$ native inclusions) corrosion starts almost immediately. The characteristic black flocculent oozes from the reaction site with inseparable effervescence of oxygen gas $O_2\uparrow$ according to the following reaction:

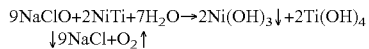

$$9NaClO+2NiTi+7H_2O \rightarrow 2Ni(OH)_3\downarrow+2Ti(OH)_4$$
$$\downarrow 9NaCl+O_2\uparrow$$

It is essential to mention that the dissolving Ni can come from two sources: from the matrix surrendering inclusion which is enriched in Ni during the process of creation of inclusion which drains Ti elements to creates inclusion as TiC or from the inclusion itself which is enriched in Ni as for example intermetallic inclusions of $Ni_4Ti_3$, $Ni_3Ti$, created for example during a wire drawing operation. But it doesn't matter from where $Ni(OH)_3$ originates both cases indicate presence of inclusions and lack of Nitinol homogeneousness.

Titanium hydroxide $Ti(OH)_4$ (white precipitate) originates when corrosion progresses is masked by the black color of $Ni(OH)_3\downarrow$, but it can also be visible by the naked eye. These two precipitates, distinguished by color, originate in the places of inclusions in the presence of NaClO: evidence that in this case Nitinol corrodes as Ti and Ni separately and not as an intermetallic compound.

Figure 1B:
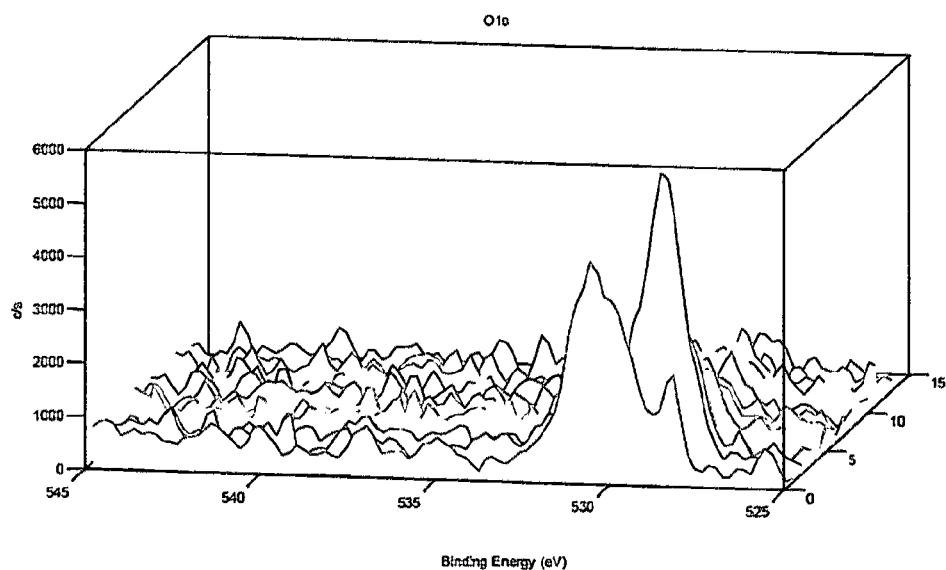
Figure 1C:
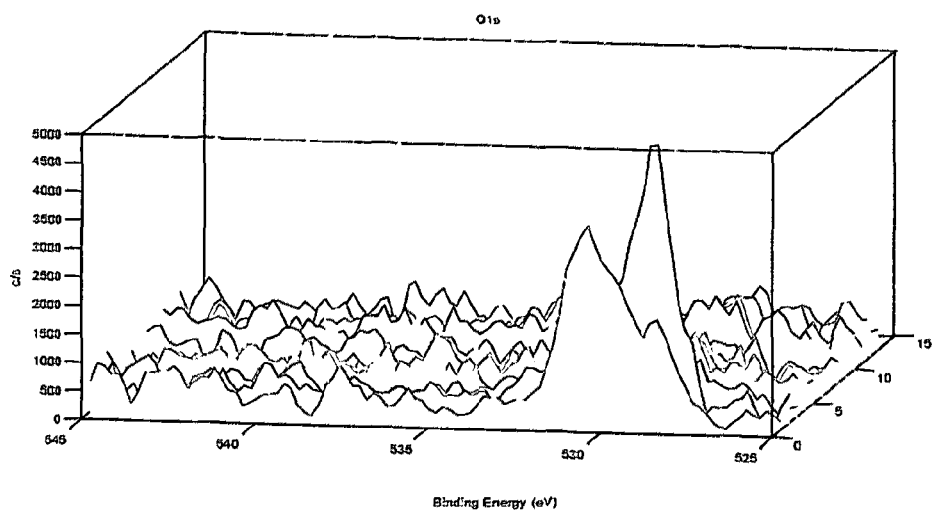
Figure 1D:
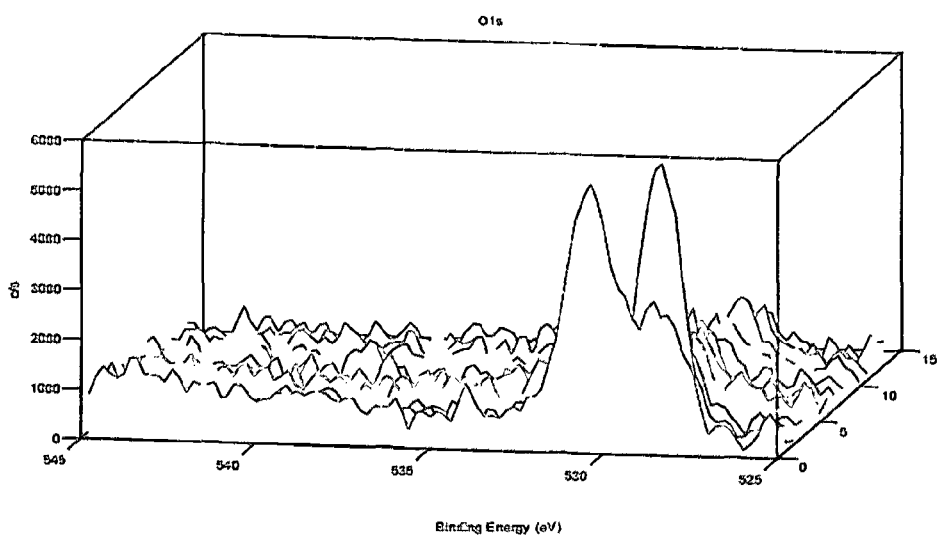

When homogenous surface inclusion-free (except titanium dioxides $TiO_2$ native inclusions) electropolished or magnetoelectropolished Nitinol implantable medical device surfaces are exposed to sodium hypochlorite (NaClO), a chemical modification of their already oxidized surface takes place. The XPS study (FIG. 1A-1D) shows oxidation enhancement of electropolished (FIG. 1B) and magnetoelectropolished (FIG. 1D) nitinol surfaces which underwent sodium hypochlorite treatment. In both cases combined oxygen signals to the depth of approximately 13 nm of oxide layer were strongest that for electropolished (FIG. 1A) and magnetoelectropolished (FIG. 1C) surfaces of Nitinol samples without sodium hypochlorite treatment and amounted to: electropolished—7800 c/s, electropolished+6% NaClO treatment—10000 c/s, magnetoelectropolished—8800 c/s, magnetoelectropolished+6% NaClO—11400 c/s correspondingly.

The strongest oxygen signals correlate with better and faster enodothelial and osteoblast cell adhesion and proliferation on electropolished and magnetoelectropolished Nitinol surfaces which underwent additional sodium hypochlorite (NaClO) treatment.

It is well recognized that that faster and better endothelialization of Nitinol implantable vascular (stent, heart valve) medical devices leads to lesser inflammation, prevents thrombus formation, minimizes chances for stent restenosis and by this speeds healing of the treated vessel.

In the last two decades a lot of methods for improving endothelialization of implantable Nitinol medical devices have been proposed with better or lesser results. These methods broadly could be divided into two groups: coating and patterning.

The coating methods depend on covering Nitinol with active or inactive substances such as: organic (polymer), inorganic (DLC—diamond like carbon, turbostratic carbon, zirconium oxide), biological (heparin, vascular or endothelium derived growth factors).

The patterning methods depend on creating a pattern or roughness with sub-micron dimensions on implantable Nitinol medical devices surfaces, with the purpose to improve adhesion, spreading and migration of endothelial cells. The patterning or roughening could be achieved by mechanical, physical, chemical or electrochemical methods.

As for successful integration of vascular Nitinol implantable devices, speed and properness of adhesion and proliferation of endothelial cell is of paramount importance. The same relates to osteoblast cells colonization and proliferation on orthopedic Nitinol implantable medical device (osseointegration).

To improve osseointegration a lot of very similar methods as for endothelialization enhancements were proposed. Some of them are: anodization, hydroxylapatite, extracellular matrix protein, fibronectin coatings etc.

The effectiveness of this proposed novel treatment for electropolished and magnetoelectropolished Nitinol surfaces which underwent 6% NaClO treatment is best shown in FIG. 2A-2D.

The micrographs of electropolished (FIG. 2B) and magnetoelectropolished (FIG. 2D) Nitinol surfaces which underwent 6% NaClO treatment show better adhesion and proliferation of osteoblast cells when compared to electopolished (FIG. 2A) and magnetoelectropolished (FIG. 2C) Nitinol surfaces without 6% NaClO treatment. Both electropolished +6% NaClO and magnetoelectropolished +6% NaClO treated Nitinol samples show almost 100% confluency which is vital for implant and bone integration.

The electropolished and magnetoelectropolished Nitinol surfaces, which underwent 6% NaClO treatment, exhibit a higher degree of endothelialization than electropolished and magnetoelectropolished Nitinol surfaces without the 6% NaClO treatment. The endothelial cells look healthier on 6% NaClO treated electropolished and magnetoelectropolished Nitinol surfaces when compared to the untreated surfaces.

To my knowledge the proposed treatment with 6% NaClO of electropolished and magnetoelectropolished Nitinol implantable medical devices for improvement of endothelialization (vascular implantable medical devices) and osseointegration (orthopedic implantable medical devices) is totally new and has never been mentioned in prior art in the field.

Sodium hypochlorite (NaClO) is an accepted liquid sterilizing agent. It kills pathogens such as Mycobacterium tuberculosis and inactivates prions. But its corrosiveness toward many metals excluded its use as sterilizer for all metallic implantable medical devices. This above generalization is incorrect. Some metals and alloys are totally immune to sodium hypochlorite and only undergo further oxidation when come in contact with it which is beneficial in the case of implantable medical devices. The best examples are titanium and Nitinol.

Misconception that sodium hypochlorite is corrosive toward Nitinol came from misunderstanding the significance of surface intermetallic inclusions which are not separable with Nitinol. Ryszard Rokicki "Detecting Nitinol Surface Inclusions" Medical Device and Diagnostic Industry, February 2010, page 44-48

The above mentions methods for enhancement of adhesion and proliferation of endothelial an osteoblast cells on electropolished and magnetoelectropolished Nitinol implantable medical devices in some cases are very complicated and impractical in application.

The simplicity, effectiveness and multi-purposiveness of described method for inclusion detection, enhancement of endothelial and osteoblast cells adhesion and proliferation and sterilization of electropolished and magnetoelectropolished Nitinol surfaces by 6% NaClO treatment should become the procedure of choice for every implantable Nitinol medical device.

The usefulness of the present invention is shown on following examples. The examples used represent only possible embodiments of the test procedure for detecting surface inclusions and enhancement of endothelial and osteoblast cell adhesion and proliferation on electropolished and magnetoelectropolished implantable Nitinol medical devices surfaces described here and should not in any way imply any restriction to the condition used here.

EXAMPLES

Example 1

Ten electropolished Nitinol guidewires were placed separately in glass tubes filled with 6% NaClO of room temperature around 25° C. Almost immediately one wire started to corrode in one place, black flocculent started to develop in corrosion site. Bubbles of oxygen were observed departing upward from corrosion site. After 15 minutes all wires were removed from 6% NaClO and rinsed with water. Visual examination of corroded wire showed a pit in place were black flocculent developed (this place was the place of Nitinol surface inclusion). The nine remaining wires have not shown signs of corrosion.

Example 2

Figure 2A:
Figure 2B:
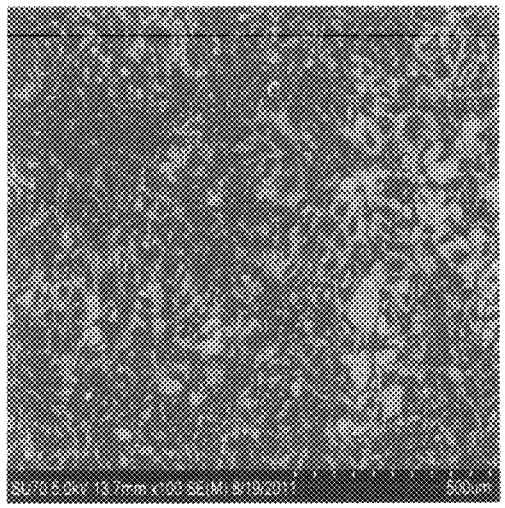
Figure 2C:
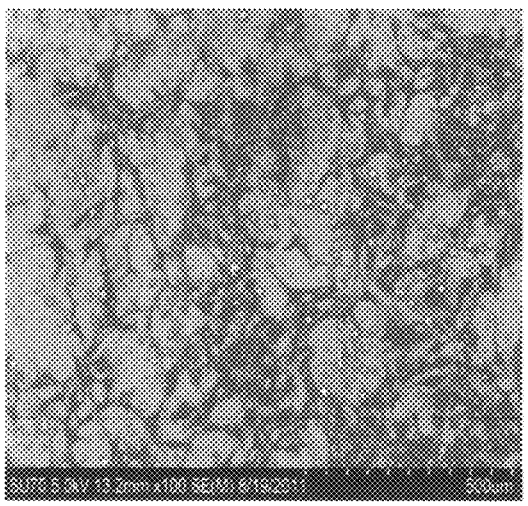
Figure 2D:
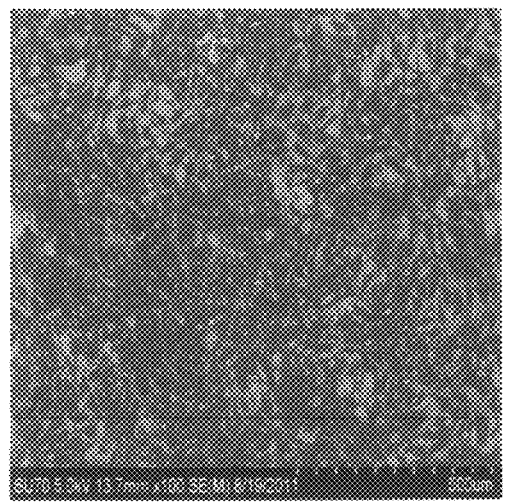

Four samples (10 mm in diameter 2 mm thick) stamped from the same plate of Nitinol were finished as follow: electropolished (EP)—FIG. 2A, electropolished (EP)+6% NaClO—FIG. 2B, magnetoelectropolished (MEP)—FIG. 2C, magnetoelectropolished (MEP)+6% NaClO—FIG. 2D. In order to assess adhesion and proliferation of osteoblast cells on differently finished Nitinol samples MC3T3 osteoblast cells were seeded and incubated for 72 hours at 37° C. After 72 hours of incubation adhesion and proliferation of MC3T3 osteoblast cell were evaluated by scanning electron microscope (SEM). At qualitative level the cells had a healthy response and have a similar morphology on all samples. However at quantitative level anybody can see profound difference between EP (FIG. 2A), MEP (FIG. 2C) and EP (FIG. 2B), MEP (FIG. 2D)+6% NaClO treated samples. EP and MEP+6% NaClO treated samples reached almost 100% confluency compared to about 40% confluency of EP and MEP samples without 6% NaClO treatment. It is worth to note that all four samples are dotted with titanium dioxide $TiO_2$ native inclusions mention previously (rounded spots). They resist dissolution during electropolishing, magnetoelectropolishing and NaClO treatment. But all four micrographs conclude harmlessness of this kind of inclusions toward osteoblast cells. As can be seen osteoblast cells adhere to those inclusions and grow on top of them.

Example 3

Four samples (10 mm in diameter and 2 mm thick) stamped from the same plate of Nitinol were finished as follows: electropolished (EP), electropolished (EP)+6% NaClO, magnetoelectropolished (MEP), and magnetoelectropolished (MEP)+6% NaClO. In order to assess adhesion and proliferation of HUVEC (human umbilical vein endothelial cells) the ISO 10993 protocols for biological evaluation of medical devices was used. After 72 hours at 37° C., 5% $CO_2$ in cell culture media Nitinol samples were gently washed with DBPS stained with Hoechst dye (to highlight the nuclei of the cells) and Mitotracker Red (to highlight the mitochondria of the cells). The samples were again incubated for 20 minutes, washed 3 times in DBPS and fixed on the sample surface with 10% formaldehyde and covered by glass slides. The qualitative and quantitative evaluation of adhesion and proliferation of endothelial cells on differently finished Nitinol samples were accomplished by using an Olympus IX81 fluorescent microscope. All of the Nitinol samples were showing good endothelial cell confluency with the highest number on the magnetoelectropolished (MEP+6% NaClO treated sample and the lowest on the electropolished (EP) sample. Taking under consideration the quality of the endothelial cell (uniformity, mitochondria development and shape) the Nitinol samples could be arranged from best to worst as follows: MEP+6% NaClO>EP+6% NaClO>MEP>EP.

The invention claimed is:

1. A method for surface inclusion detection, enhancement of endothelial and osteoblast cells adhesion and proliferation and sterilization of surfaces of electropolished and magnetoelectropolished finished products manufactured from compounds containing equal parts of nickel and titanium comprising the steps of immersing them in an aqueous solution of a chemical compound containing halogen oxyanions for a specified period of time at room temperature of around 25° C.

2. The method of claim 1, wherein said specified period of time is 7 minutes.

3. The method of claim 1, wherein said aqueous solution containing halogen oxyanions is selected from the group consisting of hypochlorite ($ClO^-$) and hypobromite ($BlO^-$).

4. The method of claim 3, wherein said hypochlorite ($ClO^-$) is sodium hypochlorite (NaClO).

5. The method of claim 4, wherein said aqueous solution containing sodium hypochlorite (NaClO) is between 1% and 12% by weight.

6. The method of claim 5, wherein said aqueous solution containing sodium hypochlorite (NaClO) is preferred to be approximately 6% by weight.

7. The method of claim 1, wherein said finished products manufactured from compounds containing equal parts of nickel and titanium are selected from the group of medical vascular and orthopedic implantable devices, medical and dental devices and instrumentation.

8. The method of claim 7, wherein said medical vascular implantable devices are bare metal stents, stent grafts, polymer covered stents, aneurysm coils, heart valves, arterial septal defect occlusion devices, IVC filters.

9. The method of claim 7, wherein said medical orthopedic devices are bone plates and screws, staples, spine fracture fixation devices, maxillofacial devices, intramedullary nails and Mitek sutures anchors.

10. The method of claim 7, wherein said medical devices and instruments are angioplasty guidewires, catheters, sutures, staples, stones and blood dot retrievers, cutting blades, endoscopes.

11. The method of claim 7, wherein said dental devices and instruments are endodontic rotary files, endodontic hand files, orthopedic archwires.

12. The method of claim 7, wherein said compounds containing equal parts of nickel and titanium are selected from the group of nickel/titanium compounds, composite nickel/titanium compounds, porous nickel/titanium compounds and thin film nickel/titanium compounds.

13. The method of claim 12, wherein said nickel/titanium compounds are fabricated by vacuum induction melting (VIM), vacuum arc melting (VAR), electron beam melting (EBM) and induction skull melting (ISM).

14. The method of claim 12, wherein said composite nickel/titanium compounds surrounds or encapsulates other metals as platinum, tantalum, gold or alloys of 90% platinum-10% nickel.

15. The method of claim 12, wherein said porous nickel/titanium compounds possesses a porosity of 8%-90% and are defined by networks of interconnected passageways extending throughout the material, which exhibits permeability permitting complete migration of fluid material throughout said network.

16. The method of claim 15, wherein said porous nickel/titanium compounds are of an independent material or in the form of a coating covering another material.

17. The method of claim 12, wherein said thin film nickel/titanium compounds are fabricated by vacuum deposition technologies or rf magnetron sputtering.

18. The method of claim 17, wherein said thin film nickel/titanium compounds are of an independent material or in the form of a coating covering another material.

\* \* \* \* \*